United States Patent [19]

Jones et al.

[11] 4,273,710

[45] Jun. 16, 1981

[54] PROCESS FOR PREPARING FLUNISOLIDE

[75] Inventors: Richard E. Jones, Palo Alto, Calif.; Jacquelyn A. Smithers, Concepcion, Chile

[73] Assignee: Syntex Corporation, Palo Alto, Calif.

[21] Appl. No.: 150,400

[22] Filed: May 16, 1980

Related U.S. Application Data

[63] Continuation-in-part of Ser. No. 40,830, May 21, 1979, abandoned.

[51] Int. Cl.$^3$ .............................................. C07J 71/00
[52] U.S. Cl. .......................................... 260/239.55 D
[58] Field of Search ................. 260/397.45, 239.55 D

[56] References Cited

U.S. PATENT DOCUMENTS 3,197,469   7/1965   Fried et al. ................. 260/239.55 D

*Primary Examiner*—Elbert L. Roberts
*Attorney, Agent, or Firm*—Tom M. Moran; Alan M. Krubiner

[57] ABSTRACT

A unique crystalline form of flunisolide is prepared by crystallizing flunisolide from a solution of an alkanol of three or four carbon atoms, e.g. n-butanol, containing 0.2 to 5%, preferably 1.0 to 4.0% by volume water.

6 Claims, No Drawings

PROCESS FOR PREPARING FLUNISOLIDE

This is a continuation-in-part of application Ser. No. 040,830, filed May, 21, 1979, now abandoned.

FIELD OF THE INVENTION

This invention relates to a process for making a unique crystalline form of flunisolide (hereafter Form A).

PRIOR ART

Flunisolide is the United States adopted name for 6α-fluoro-11β,21-dihydroxy-16α,17α-isopropylidenedioxypregna-1,4-diene-3,20-dione. The class of compounds to which flunisolide belongs and procedures for preparing them are described in U.S. Pat. No. 3,126,375 to Ringold et al. These compounds exhibit anti-inflammatory and anti-pyretic activity and have primary utility in the treatment of topical inflammation. Flunisolide may also be formulated with pharmaceutically acceptable aerosol propellants and used to treat respiratory conditions such as asthma, allergic rhinitis, etc. in mammals (see, for example, Belgian Patent No. 842,192). One particular polymorphic form (Form A, a hemihydrate) of flunisolide has been found to be particularly stable in the presence of aerosol propellant formulations and therefore is preferred (see the aforementioned Belgian Patent No. 842,192). However, because of the ability of flunisolide to form various polymorphic forms as well as to form crystal habits which include some of the solvents from which the product is crystallized, a process must be employed which reproducibly gives the desired Form A of flunisolide.

In U.S. Pat. No. 3,126,375 to Ringold et al solvents used for crystallization of the family of steroids of which flunisolide is a member include such solvents as ethyl acetate and methanol. However, when these solvents are used to recrystallize flunisolide it is found that generally flunisolide forms a clathrate, solvate, or related solvent inclusion complex with these solvents. Such crystal forms of flunisolide are unacceptable because of the uniformity required for a pharmaceutically acceptable aerosol formulation.

In Belgian Patent No. 842,192 a process is disclosed for preparing Form A of flunisolide. However, that particular process employs halogenated hydrocarbons which have some undesirable properties.

SUMMARY AND PREFERRED EMBODIMENTS

It has now been found that Form A of flunisolide (a hemihydrate) can be reproducibly obtained by the process of this invention. The process comprises crystallizing flunisolide from an aqueous solution of an alkanol of three or four carbon atoms. The crystals formed in this manner reproducibly exhibit Form A, crystalline flunisolide. This is surprising, especially in view of the fact that if one recrystallizes flunisolide from an aqueous solution of methanol or ethanol one does not obtain Form A.

The unique crystalline form of flunisolide which is prepared by the process of this invention is a hemihydrate, crystalline flunisolide, 6α-fluoro-11β,21-dihydroxy-16α,17α-isopropylidenedioxypregna-1,4-diene-3,20-dione and is referred to herein as Form A. The crystalline structure has a powder X-ray diffraction pattern as indicated in Table A, below.

TABLE A

| d<br>A | $I/I_1$<br>% | Θ<br>deg. |
|---|---|---|
| 10.04 | 50 | 4.4 |
| 9.82 | 60 | 4.5 |
| 9.30 | 80 | 4.8 |
| 7.69 | 50 | 5.8 |
| 6.91 | 50 | 6.4 |
| 6.32 | 10 | 7.0 |
| 5.98 | 90 | 7.4 |
| 5.53 | 100 | 8.0 |
| 5.21 | 60 | 8.5 |
| 5.06 | 60 | 8.8 |
| 4.79 | 10 | 9.3 |
| 4.55 | 70 | 9.8 |
| 4.33 | 1 | 10.3 |
| 4.13 | 10 | 10.8 |
| 3.95 | 10 | 11.3 |
| 3.86 | $5_b$ | 11.5 |
| 3.70 | $5^b$ | 12.0 |
| 3.63 | 10 | 12.3 |
| 3.36 | 1 | 13.3 |
| 3.30 | 2 | 13.5 |
| 3.21 | 2 | 13.9 |
| 3.03 | 1 | 14.8 |
| 2.88 | 2 | 15.5 |
| 2.67 | $2_b$ | 16.8 |
| 2.63 | $1^b$ | 17.0 |
| 2.60 | 1 | 17.3 |
| 2.56 | 1 | 17.5 |
| 2.40 | 3 | 18.8 |
| 2.31 | 1 | 19.5 |
| 2.28 | 1 | 19.8 |
| 2.13 | 1 | 21.3 |
| 2.10 | 1 | 21.5 |
| 1.97 | 1 | 23.0 |
| 1.88 | 2 | 24.3 |

$b$ = broad line due to failure to resolve two closely spaced lines.

A general discussion of the theory and definitions as well as the general procedure of X-ray diffractometry is set forth in the monograph at pages 902–904 of the National Formulary, XIII.

The above X-ray diffraction pattern was obtained in accordance with the method described in Belgian Patent No. 842,192.

Form A of flunisolide is further characterized by the presence of 2.0±0.2 percent (%) by weight water. Because the calculated stoichiometric value of the percentage of water by weight for a hemihydrate of flunisolide is 2.03%, it appears that Form A is a hemihydrate.

Analysis of Form A for water content is done by any suitable analytical method. Generally analysis is done using Karl Fischer reagent. The Karl Fischer analysis for water may be performed according to the original method set forth in Angewandte Chemie, 48, 394 (1935). Preferably, however, the analysis is performed using Photovolt Corporation's automatic analyzer, Aquatest IV. The aquatest IV is a coulometric titrator which incorporates microprocessor control and is based on the specific and quantitative reaction of water with Karl Fischer reagent. The instrument is unique in that the reagent is generated electrically which eliminates the need for standardization or calibration. The accuracy of the instrument is within ±10 micrograms (mcg) or 1% which ever is greater. For determination of water in flunisolide Form A, where the sample sizes chosen for the determinations are between 35 mg and 75 mg and contain between 700 mcg and 1500 mcg of water, the accuracy is within ±0.03% of the amount of water determined in mcg.

The microprocessor control serves to distinguish between the titration of water which is in the sample and any reaction of the Karl Fischer reagent with other entities such as aldehydes or ketones. The Aquatest IV is operated as described in the instruction manual published by Photovolt Corporation in July 1978 and by Paper No. 260 presented at the Pittsburg Conference on Analytical Chemistry and Applied Spectroscopy in February of 1978 by K. A. Lindblom. The address of Photovolt Corporation is 1115 Broadway, New York, New York 10010.

In the process of this invention it is important that the equipment that is used for the crystallization of flunisolide is completely clean. If there is another polymorphic form of flunisolide present in the flask or container in which the crystallization takes place the desired form A may be contaminated with another phase which is formed simultaneously due to the crystallization which is directed by the existing crystals of flunisolide. Thus, before performing the process of the invention it is wise to wash all equipment thoroughly with the alkanol to be used, e.g. aqueous n-butanol, to assure that any extraneous flunisolide of a different crystal form is completely removed from the equipment.

As pointed out previously, the process of the invention comprises crystallizing flunisolide from an aqueous solution of an alkanol of three or four carbon atoms. Alkanols of 3 or 4 carbon atoms include, for example, isopropyl alcohol, n-propanol, n-butanol, isobutyl alcohol, sec-butyl alcohol, tert-butyl alcohol. N-butanol is preferred. The alkanol is aqueous, that is, it contains about 0.2 to 5% water by volume, and preferably contains 1 to 4% water by volume. With n-butanol, about 2.3% by volume is used.

The flunisolide solution can be obtained in several ways. Any polymorphic form of flunisolide can be added to the alkanol or the alkanol can be added to the crystalline form and agitated until the flunisolide is entirely in solution. Thereafter, the desired amount of water can be added. However, for the preparation of the solution, aqueous alkanol also can be used. In order to speed the process of solution the alkanol can be heated to a temperature of 75° C. or more, up to its boiling point (e.g. for n-butanol 117° C.). Alternatively, the alkanol can be added to an existing solution of flunisolide in another solvent with a lower boiling point than the alkanol. For example, n-butanol can be added to a solution of flunisolide in methylene chloride and the methylene chloride distilled off while n-butanol becomes the solvent for flunisolide. This is done through replacement distillation. It is important of course, to use sufficient alkanol to keep the flunisolide in solution. Thereafter, water is added. Thus, the concentration of flunisolide will vary with the alkanol used. It has been found that about 50 grams of flunisolide will dissolve at 80° C. in 250 milliliters (ml) of n-butanol containing 2% v/v water and crystallize from solution at about 35° C. and give the new crystalline form A.

Once a solution of flunisolide in the alkanol is obtained, the crystallization of the flunisolide is effected, preferably at a temperature of less than about 75° C. For example, this can be done by allowing an n-butanol solution to slowly cool, e.g., at a rate of 1° every 30 seconds to about 10 minutes. The initial temperature of the aqueous alkanol solution can be anywhere from about 30° C. to about the boiling point of the alkanol.

Although the desired Form A of flunisolide is obtained by allowing the crystallization through cooling alone, such a process may not always be economically advantageous because of the large amount of flunisolide remaining in solution. On a small scale, a suitable alkane solvent (in which flunisolide has little solubility) may be added to the alkanol solution to force the flunisolide from solution. The alkane solvent is preferably n-hexane or n-heptane. Generally the volume of n-hexane or n-heptane which is added is about twice to about five times the volume of the alkanol solution, and is added slowly to the alkanol solution containing about 50 g. of flunisolide over an extended period of time, e.g. about 10 minutes to 4 hours or more, depending on the volumes of the solvents involved. For example, 750 ml of n-hexane may be added to about 250 ml of an aqueous n-butanol flunisolide solution over an hour. The alkane solvent may be at the same temperature as the n-butanol solution, or less, but preferably is at ambient temperature, i.e., about 20°–25° C. to speed the crystallization.

Once the steroid crystals are obtained, they are dried by means known in the art such as vacuum drying to remove any solvent. This may be done for a period of 2 hours to several days.

The unique crystalline structure of flunisolide having the X-ray diffraction pattern of Table A can be distinguished from other polymorphic forms of flunisolide using, i.a., analysis by X-ray powder diffraction, differential scanning calorimetry, polarized light microscopy, water analysis and hot stage microscopy.

The following examples are given to further set forth specific, representative conditions for the process of the invention but are not to be interpreted as limiting the scope of the claims appended hereto.

EXAMPLE 1

Fifty (50) grams (g) of damp flunisolide (containing about 1% by weight water) are placed in a 1 liter Erlenmeyer flask provided with magnetic stirring, and 250 milliliters (ml) of n-butanol containing about 0.1% by volume water is added. The mixture is heated to 70° until complete dissolution is achieved and then the solution is left to cool slowly at approximately 1 degree per minute. At about 35° C. crystallization becomes apparent and at 30° C. n-heptane is slowly added over a period of about 1 hour until the total volume of the mixture is 1 liter. After stirring for a further hour at ambient temperature, the product is filtered, washed several times with n-heptane and air dried. The material is then dried in a vacuum oven at 50° C. for three days to yield 45 grams of flunisolide having a powder X-ray diffraction pattern set forth in Table A.

Analysis of the crystals using Karl Fischer reagent in Photovolt's Aquatest IV gives 1.93% water.

EXAMPLE 2

One hundred (100) grams of flunisolide are placed in a 500 ml Erlenmeyer flask provided with magnetic stirring, and 196 ml analytical grade n-butanol and 4 ml distilled water are added. The mixture is heated with stirring to 95° C. until complete dissolution is achieved, then cooled with stirring. At about 70° crystallization becomes apparent. The resulting slurry is cooled to room temperature and stirred overnight. The product is then filtered and air-dried, yielding 85 g. flunisolide having the powder X-ray diffraction pattern set forth in Table A.

Analysis of the resulting crystals using Karl Fischer reagent in Photovolt's Aquatest gives 1.93% w/water.

EXAMPLE 3

Ten (10) grams of flunisolide are placed in a 50 ml Erlenmeyer flask provided with magnetic stirring and 15 ml n-propanol plus 0.6 ml distilled water added. The mixture is heated with stirring to 90° C. until complete dissolution is achieved, then cooled with stirring. Crystallization becomes apparent at about 60° C., and the resulting slurry is cooled with stirring to room temperature. After overnight stirring at room temperature, the product is filtered and air dried, giving 8.6 g flunisolide having the powder X-ray diffraction pattern set forth in Table A.

Analysis of the crystals using Karl Fischer reagent in Photovolt's Aquatest IV gives 2.08% w/water.

EXAMPLE 4

Ten (10) grams flunisolide are placed in a 50 ml Erlenmeyer flask equipped with magnetic stirring and 20 ml isopropyl alcohol and 1 ml distilled water added. This mixture is heated to about 70° C. until a clear solution is obtained, then cooled with stirring. Crystallization becomes evident at 50°–60° C. The resulting slurry is cooled to room temperature and stirred overnight. After standing for 6 days at room temperature, filtering, air drying, drying in vacuo at room temperature for 24 hours, 8.5 g of flunisolide is obtained having the powder X-ray diffraction pattern set forth in Table A.

Analysis of the crystals using Karl Fischer reagent in Photovolt's Aquatest IV gives 2.18% water.

EXAMPLE 5

Two (2) grams of flunisolide having the X-ray diffraction pattern set forth in Table A are added to a flask containing 10 ml of 95% ethanol at room temperature. The mixture was heated with stirring until all of the material is entirely dissolved. The resulting solution was then allowed to cool to room temperature while scratching the sides of the flask with a glass rod to induce crystallization. The crystals obtained were analyzed using polarized light microscopy and were found to be different than the flunisolide used initially.

EXAMPLE 6

The procedure of Example 5 was repeated except that crystallization was induced by seeding with a small amount of flunisolide having the X-ray diffraction pattern of Table A. The resulting crystals so obtained were analyzed using polarized light microscopy and were found to differ from the flunisolide used as seed crystals.

EXAMPLE 7

Fifty (50) grams of flunisolide were added to 600 ml methanol and heated to dissolve all the flunisolide, then allowed to cool. The volume of the resulting solution was reduced by half on a rotary evaporator, then the resulting slurry was filtered and crystalline flunisolide isolated. The filtrate was again evaporated down to approximately 60 ml. volume, then filtered again as above. The resultant material was air dried, giving 26 gms of flunisolide which differs (as analyzed via X-ray diffractometry, differential scanning calorimetry, visual thermal analysis, and weight loss on heating of 2.6%) from that having the X-ray diffraction pattern set forth in Table A.

EXAMPLE 8

One hundred (100) mg flunisolide was dissolved in 20 ml absolute ethanol at approximately 70° C. The resulting solution was cooled to room temperature and allowed to evaporate over a three day period. The resultant crystalline flunisolide was collected, analyzed by X-ray diffractometry, differential scanning calorimetry, visual thermal analysis, and weight loss on heating (4.5, 4.9%). The resulting crystalline flunisolide was found to differ from the crystalline flunisolide exhibiting the X-ray diffraction pattern on Table A.

EXAMPLE 9

Ten (10) grams flunisolide are placed in a 50 ml Erlenmeyer flask equipped with magnetic stirring and 20 ml t-butyl alcohol and 1 ml distilled water added. This mixture is heated until a clear solution is obtained then cooled with stirring until crystallization becomes evident. The resulting slurry is cooled to room temperature and stirred overnight. The resulting mixture is filtered, air dried and dried in vacuo at room temperature for 24 hours to give flunisolide having the powder X-ray diffraction pattern set forth in Table A.

Analysis of the crystals using Karl Fischer reagent in Photovolt's Aquatest IV gives about 2% by weight water.

The subject matter claimed is:

1. A process for preparing a crystalline form of flunisolide which contains 2.0±0.2% by weight water exhibits an X-ray diffraction pattern as set forth in Table A.

TABLE A

| d A | I/I$_1$ % | Θ deg. |
|---|---|---|
| 10.04 | 50 | 4.4 |
| 9.82 | 60 | 4.5 |
| 9.30 | 80 | 4.8 |
| 7.69 | 50 | 5.8 |
| 6.91 | 50 | 6.4 |
| 6.32 | 10 | 7.0 |
| 5.98 | 90 | 7.4 |
| 5.53 | 100 | 8.0 |
| 5.21 | 60 | 8.5 |
| 5.06 | 60 | 8.8 |
| 4.79 | 10 | 9.3 |
| 4.55 | 70 | 9.8 |
| 4.33 | 1 | 10.3 |
| 4.13 | 10 | 10.8 |
| 3.95 | 10 | 11.3 |
| 3.86 | 5$_b$ | 11.5 |
| 3.70 | 5 | 12.0 |
| 3.63 | 10 | 12.3 |
| 3.36 | 1 | 13.3 |
| 3.30 | 2 | 13.5 |
| 3.21 | 2 | 13.9 |
| 3.03 | 1 | 14.8 |
| 2.88 | 2 | 15.5 |
| 2.67 | 2$_b$ | 16.8 |
| 2.63 | 1 | 17.0 |
| 2.60 | 1 | 17.3 |
| 2.56 | 1 | 17.5 |
| 2.40 | 3 | 18.8 |
| 2.31 | 1 | 19.5 |
| 2.28 | 1 | 19.8 |
| 2.13 | 1 | 21.3 |
| 2.10 | 1 | 21.5 |
| 1.97 | 1 | 23.0 |
| 1.88 | 2 | 24.3 | which process comprises crystallizing said steroid from a solution of said steroid in a liquid alkanol of three or four carbon atoms containing 0.2 to 5% water by volume.

2. The process of claim 1 wherein said solution contains 1 to 4% water by volume.

3. The process of claim 1 or 2 wherein said alkanol is n-butanol.

4. The process of claim 1 or 2 wherein said alkanol is isopropyl alcohol or n-propyl alcohol.

5. The process of claim 1 or 2 wherein said alkanol solution is allowed to cool from a temperature above 75° C. to a temperature below 75° C. at which crystallization takes place.

6. The process of claim 5 wherein said solution is cooled to a temperature below 30° C.

* * * * *